United States Patent [19]

Lars et al.

[11] Patent Number: 5,085,223
[45] Date of Patent: Feb. 4, 1992

[54] MINIATURIZED PRESSURE SENSOR HAVING MEANS FOR PROTECTION OF DIAPHRAGM

[75] Inventors: Tenerz Lars, Ringgatan; Hök Bertil, Sportfiskargatan; Lonc Roman; Hammarström Ola, both of Flogstavägen; Engström Tomas, Karlsrogatan, all of Sweden

[73] Assignee: Radi Medical Systems AB, Uppsala, Sweden

[21] Appl. No.: 469,555

[22] PCT Filed: Jul. 28, 1989

[86] PCT No.: PCT/SE89/00422
§ 371 Date: Mar. 28, 1990
§ 102(e) Date: Mar. 28, 1990

[87] PCT Pub. No.: WO90/01294
PCT Pub. Date: Feb. 22, 1990

[30] Foreign Application Priority Data

Jul. 29, 1988 [SE] Sweden .................... 8802765

[51] Int. Cl.⁵ .................................. A61B 5/02
[52] U.S. Cl. ........................ 128/675; 128/637; 128/748; 73/715; 73/706
[58] Field of Search ............ 128/637, 672, 673, 675, 128/748; 73/715, 861.47, 705, 706, 714, 726, 727, 756

[56] References Cited

U.S. PATENT DOCUMENTS

| | | | |
|---|---|---|---|
| 3,550,583 | 12/1970 | Chiku | 128/675 |
| 4,274,423 | 6/1981 | Mizuno et al. | 128/675 |
| 4,456,013 | 6/1984 | De Rossi et al. | 128/675 |
| 4,603,699 | 8/1986 | Himpens | 128/673 |
| 4,722,348 | 2/1988 | Ligtenberg et al. | 128/675 |
| 4,735,212 | 7/1988 | Cohen | 128/675 |
| 4,748,986 | 6/1988 | Morrison et al. | 128/772 |
| 4,873,986 | 3/1989 | Wallace | 128/675 |

FOREIGN PATENT DOCUMENTS

| | | |
|---|---|---|
| 0241294 | 10/1987 | European Pat. Off. . |
| 0263190 | 4/1988 | European Pat. Off. . |
| 2206624 | 8/1972 | Fed. Rep. of Germany . |
| 88/00023 | 1/1988 | Int'l Pat. Institute . |

*Primary Examiner*—Stephen C. Pellegrino
*Assistant Examiner*—Robin R. Longo
*Attorney, Agent, or Firm*—Foley & Lardner

[57] ABSTRACT

A miniaturized transducer for in vivo measurements of physiological pressure has a transducer unit and an inner tube with a wall opening. A diaphragm covers the wall opening. Distinguishing for the invention is that the diaphragm is protected by an outer tube arranged outside the inner tube, and having a wall opening situated radially opposite the wall opening of the inner tube. An end closure closes off the distal end of the tube and a seal seals the outer tube against the inner tube. The lumen of the inner tube is in communication with the atmospheric pressure.

10 Claims, 2 Drawing Sheets

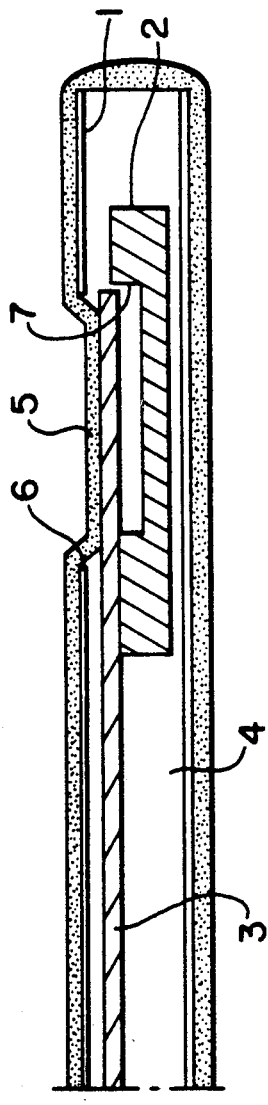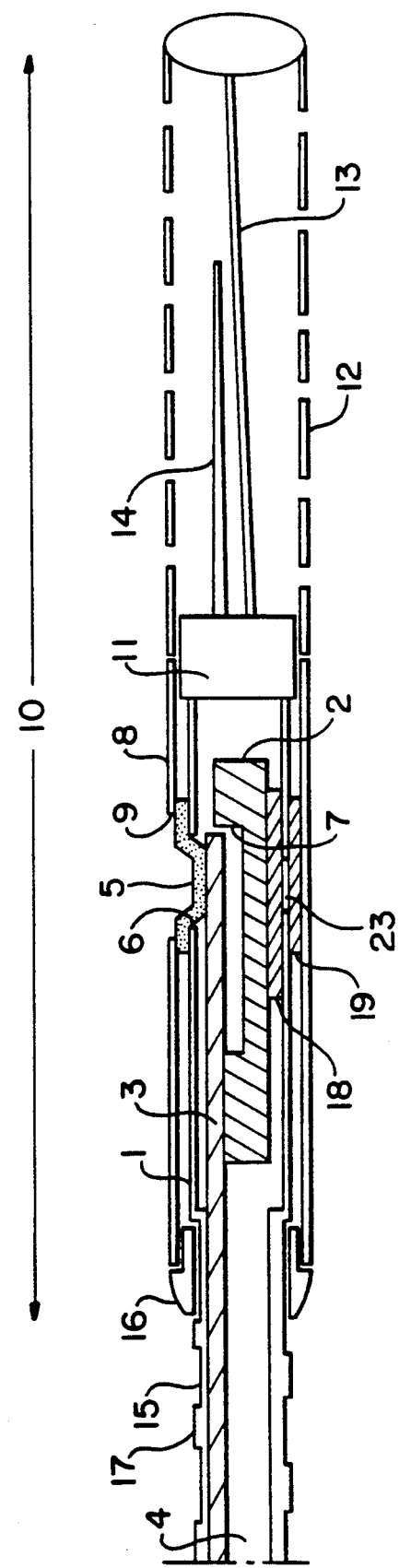

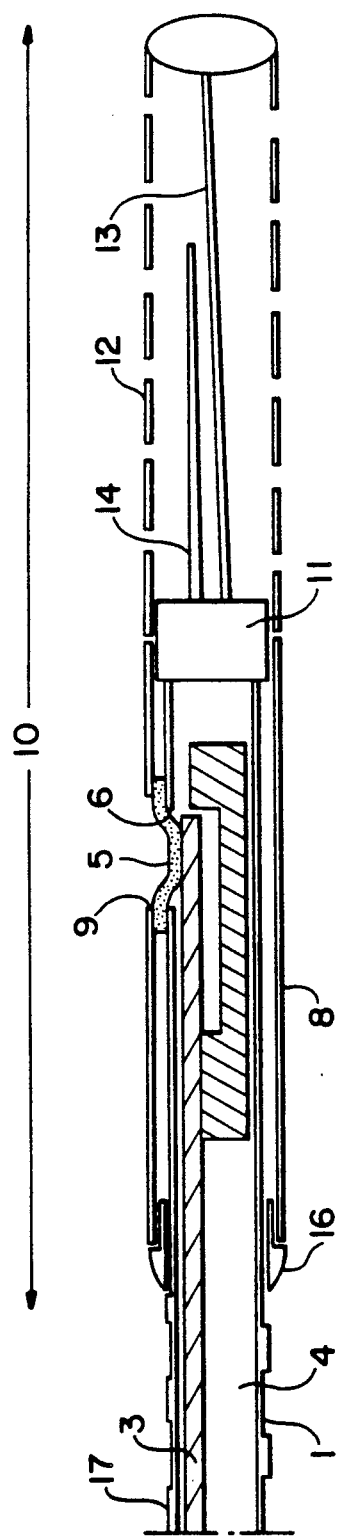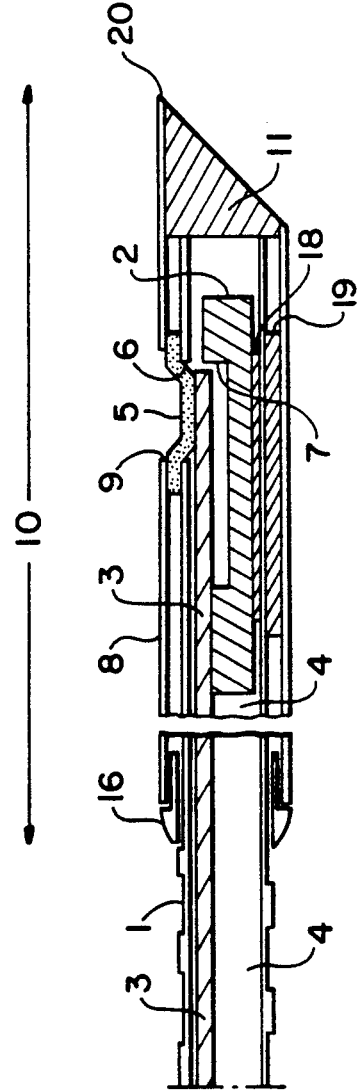

MINIATURIZED PRESSURE SENSOR HAVING MEANS FOR PROTECTION OF DIAPHRAGM

The present invention relates to a miniaturized pressure transducer used to measure in vivo physical pressure. An example of such a use is the insertion of the transducer into the vena cava to obtain a bloodless measurement of the pressure in the coronary vessel.

Pressure transducers of the kind mentioned above are known from our International Patent Application WO 88/00023. Such a known transducer is illustrated in FIG. 1, and includes an inner tube 1 within which a pressure transducer element comprising a silicon wafer 2 and an light conductor 3 is inserted. The lumen 4 of the tube is in communication with the atmospheric pressure. The distal part of the inner tube 1 is completely surrounded by a diaphragm 5. The inner tube has an opening 6 covered by the diaphragm. The diaphragm is mechanically affected by the physical pressure which is to be measured, and its movements are transferred to the light conductor 3. The amount of light reflected from the flat surface 7 of the silicon wafer 2 and picked up by the light conductor 3 is proportional to the physical pressure which is to be measured.

A disadvantage of the known structure is that the diaphragm is unprotected and is subject to the risk of damage including the possibility that the diaphragm material could be torn away from the tip of the transducer.

The risk of damage to the diaphragm is particularly likely to occur in the case where the transducer, which has an outer diameter in the order of magnitude 0.5 mm, is inserted in a catheter which is used to perforate the tissue in which the pressure is to be measured.

The present invention has the object of providing a solution to the above-mentioned problem.

The diaphragm must meet certain mechanical requirements. It must be impermeable, flexible and not dependent on temperature. As the flexibility of the diaphragm material increases the resolution of the pressure signals will be better. Thus, in the known pressure transducer, a compromise must be made between the mechanical flexibility and the mechanical tearing strength of the diaphragm material.

The pressure transducer itself is subject to certain demands regarding its exterior dimensions. Its outside diameter should, therefore not exceed about 0.46 mm, and its axial length should be short, hardly longer than about 4 mm.

The above mentioned problem is solved, in accordance with the invention, with mechanically protecting the diaphragm by an outer tube. The outer tube is placed over the inner tube and has a wall opening situated directly opposite the wall opening of the inner tube. The diaphragm, the thickness of which can be then reduced considerably, is fixed between the outer and inner tubes, and only the part of which is exposed by the opening of the outer tube can be subjected to damage. This exposed diaphragm surface is considerably less than the exposed diaphragm surface in the embodiment shown in FIG. 1.

The arrangement of an outer tube having an outside diameter not greater than 0.46 mm has been enabled by the miniaturization of the silicon wafer 2 and by a reduction of the diameter of the light conductor 3, as compared to the pressure transducer described in WO 88/00023.

Since the exposed diaphragm surface is considerably reduced, the tearing strength requirement for the diaphragm material is also considerably reduced, thereby making, for use in the pressure transducer considerably more types of diaphragm material than was previously the case. Thus it will be possible to use diaphragm material which is soft and which gives rise to high-resolution signals.

Different embodiments of the invention will now be described from the following detailed description, and in connection with the accompanying drawings, wherein FIG. 1 is a longitudinal section of a known miniaturized pressure transducer, FIG. 2 is a longitudinal section of a first embodiment of the pressure transducer in accordance with the invention, FIG. 3 is a longitudinal section of a second embodiment of the pressure transducer in accordance with the invention, FIG. 4 is a longitudinal section of a third embodiment of the invention, and FIG. 5 is an end view of the tip of the embodiment in accordance with FIG. 4.

The pressure transducer in FIG. 2 includes an inner tube 1, a silicon wafer 2, an optical fibre 3, in which the wafer and fibre move together in the lumen 4 of the inner tube 1. The diaphragm, which is here much smaller than the one in FIG. 1, covers the opening 6 in the inner tube 1. An outer tube 8, with a wall opening 9, is arranged outside the inner tube and is coaxial therewith. The openings 6 and 9 are radially opposite each other and the diaphragm is fixed between the outer tube 8 and inner tube 1 in the area around the openings. The outer tube 8 is arranged in the distal part 10 of the pressure transducer. A distal end cap 11 seals the distal ends of the inner and outer tubes 1 and 8 making them pressure-tight. A helix 12 is anchored in the end closure 11 and extends forward in the longitudinal direction of the tube. A safety thread 13 extends between the forward end of the helix 12 and the end cap 11. The object of the safety thread is to ensure that if the helix 12 loosens from the end cap 11, the helix will accompany the transducer when it is pulled up out of the body, and also to ensure that the turns of the helix will not be extended to a greater extent than is permitted when the transducer is pulled backwards. A core filament 14 is anchored in the end closure 11 and is preferably tapered.

The helix 12 surrounds the core filament 14. The helix 12 can be bent backwards over itself, and the task of the core filament 14 is to increase the bending resistance of the helix for increasing amounts of such backward bending.

The inner tube 1 is connected at its proximal end to a thin tube 15 which is in communication with the atmospheric pressure. The joint between the thin tube 15 and the inner tube 1 is inside the proximal end of the outer tube 8. So that the tube 15 will not crumple, when the pressure transducer is taken through veins and arteries it has a dimension-stabilizing helix ribbon 17 wound around its outer surface. The outer tube 8 has an annular joint 16 in which the thin tube 15 is fitted. This joint 16 is arranged in the proximal end of the outer tube and is sealed by welding, soldering or glueing.

The unit formed by the optical fibre 3 and silicon wafer 2 is glued to the interior wall of the inner tube 1 as illustrated by glued joint 18. The inner tube 1 is, in turn, glued against the interior wall of the outer tube 8, as illustrated by glued joint 19. An optional, wall opening 23 for glue can be made in the inner tube 1 to allow glueing of the unit comprising the optical fibre 3 and the silicon wafer 2.

The inner tube 1 and the thin tube 15 can be joined to each other using a welding technique. According to an alternative embodiment, the tube 1 which is wider than the tube 15, can be made integral with the narrower tube 15 by making them from a single piece of material using an etching technique.

In accordance with another embodiment of the invention as illustrated in FIG. 3, the tubes 1 and 15 are designed as one piece having the same inside and outside diameters. The length of the distal part 10 is here only 4 mm here and the outside diameter D is 0.46 mm.

In the embodiment shown in FIGS. 4 and 5, the flexible tip formed by the details 12-14 in the embodiments according to FIGS. 1-3, is replaced by a stiff facet-ground tip 20 used for penetrating tissue in which pressure is to be measured. The tip is formed by facet-grinding the end closure 11 and the outer tube 8. An example of the edges 21 produced after the grinding of the tip is illustrated in FIG. 5.

In the embodiments described above, the diameter of the optical fibre 3 is 0.125 mm or less. The wall opening 9 is substantially rectangular, as seen in plan from above. The dimensions of the wall opening are in the order of magnitude of about 0.5×0.2 mm.

The outer tube 8 is preferably made of steel treated with teflon (i.e. a steel tube with an outer coating of teflon). The inner tube 1 is also preferably made from steel. The inside diameter of the outer tube 8 is about 0.35 mm and the outside diameter of the inner tube is about 0.3 mm making the thickness of the diaphragm 5 being in an order of magnitude of about 0.05 mm. Many different diaphragm materials can be used, among these being silicone rubber and latex. The diaphragm is retained between outer and inner tubes by being squeezed in and/or by being glued between the tubes. The end closure 11 and joint 16 are made by either glueing or soldering. Silver or tin are used as solder.

The embodiments described above can be modified within the scope of the inventive concept.

We claim:

1. A miniaturized pressure transducer assembly, comprising:
    an outer tube;
    an inner tube disposed coaxially therein, thereby defining an annular space therebetween, said inner tube being in communication with atmospheric pressure;
    an annular joint located between a proximal end of said outer tube and an exterior wall of said inner tube;
    said inner and outer tubes each having a cooperating aperture defined near distal ends thereof;
    a diaphragm filling said aperture, said diaphragm being disposed in said annular space;
    a pressure transducer unit disposed within said inner tube, said pressure transducer unit moved by a movement of said diaphragm; and
    a distal end cap attached to said inner and outer tubes.

2. Transducer as claimed in claim 1, comprising a helix ribbon which is wound around the outer tube.

3. A transducer as claimed in claim 1, wherein said inner tube has first and second tubular portions, said first portion having an inner diameter greater than an outer diameter of said second portion.

4. Transducer as claimed in claim 3, wherein said inner tube has a joint between said first and second portions, said portions located inside the outer tube.

5. Transducer as claimed in claim 3, comprising a helix ribbon which is wound around said inner tube.

6. Transducer as claimed in claim 1, comprising a glue joint between said transducer unit is glued and an inner wall of said inner tube, said exterior wall of said inner tube connected to an inner wall of said outer tube.

7. Transducer as claimed in claim 1, wherein said inner tube has an additional wall aperture.

8. Transducer as claimed in claim 1, comprising a helix arranged at the distal end cap, said helix projecting forwards in the longitudinal direction of said tubes; a safety thread anchored at one end in a distal end part of the helix and at another end in the end cap; a tapered core filament arranged inside the helix, a larger end of said filament anchored in the distal end cap with a tip cantilevering out from the end cap.

9. Transducer as claimed in claim 1, wherein the end cap has a facet-ground tip.

10. Transducer as claimed in claim 1, comprising a helix ribbon which is wound around said inner tube.

* * * * *